US00PP31002P2

(12) United States Plant Patent
Olesen

(10) Patent No.: US PP31,002 P2
(45) Date of Patent: Nov. 5, 2019

(54) MINIATURE ROSE PLANT NAMED 'POULPAH079'

(50) Latin Name: ***Rosa* hybrid**
Varietal Denomination: Poulpah079

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,576

(22) Filed: Sep. 4, 2018

(51) Int. Cl.
*A01H 5/02* (2018.01)
*A01H 6/74* (2018.01)

(52) U.S. Cl.
USPC ..... Plt./119
CPC ..... *A01H 6/74* (2018.05); *A01H 5/02* (2013.01)

(58) Field of Classification Search
USPC ..... Plt./119, 118
CPC ..... A01H 5/0222
See application file for complete search history.

(56) References Cited

PUBLICATIONS https://www.helpmefind.com/rose/l.php?I=2.70852.0; No date; 1 page.*

* cited by examiner

*Primary Examiner* — Kent L Bell

(57) ABSTRACT

A new garden rose plant of the Miniature class which has abundant, orange yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah079'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpah079', originated as a single seedling from the stated cross.

The new variety may be distinguished from its male pollen parent and female seed parent primarily by the following characteristics. The male pollen parent plant has light apricot flowers while the new variety has orange flowers. The female seed parent plant has a growth height of 100 cm, while the new variety has a growth height of 40 cm.

The objective of the hybridization of this rose variety was to create a new and distinct variety with unique qualities, such as:

1. Uniform and abundant orange yellow flowers;
2. Vigorous, but compact growth when propagated on its own roots;
3. Exceptional disease resistance.

This combination of qualities is not present in previously available commercial cultivars of this type, known to the inventor, and distinguish 'Poulpah079' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpah079' was selected in the spring of 2008 by the inventor as a single plant from the progeny of the aforementioned hybridization.

Asexual reproduction of 'Poulpah079' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpah079' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah079'.

Specifically illustrated in FIG. 1 of the drawings are open flowers viewed from above and the side, flower bud, flower petals detached, and sepals detached showing reproductive flower parts.

Figure 1:
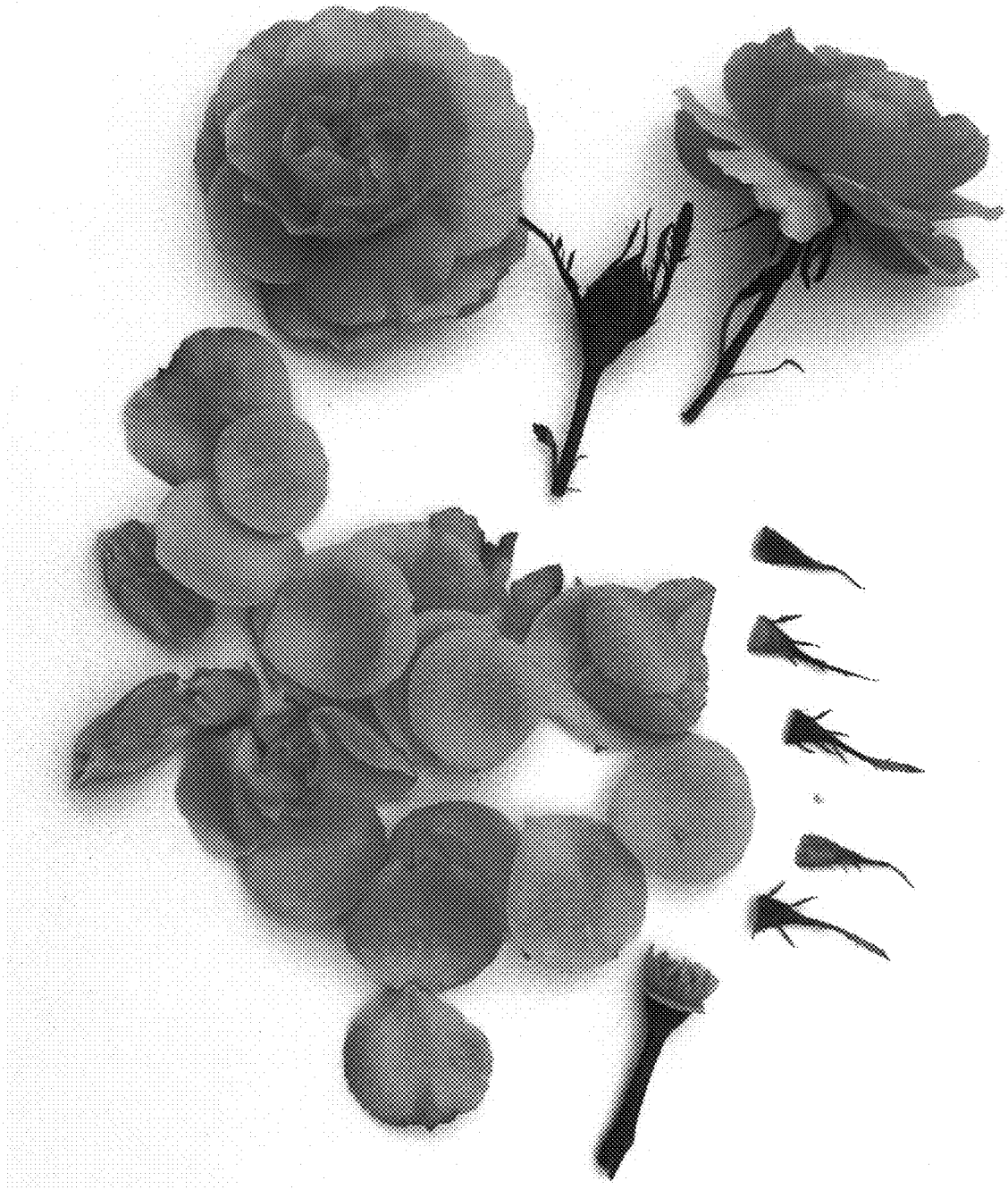
Figure 2:
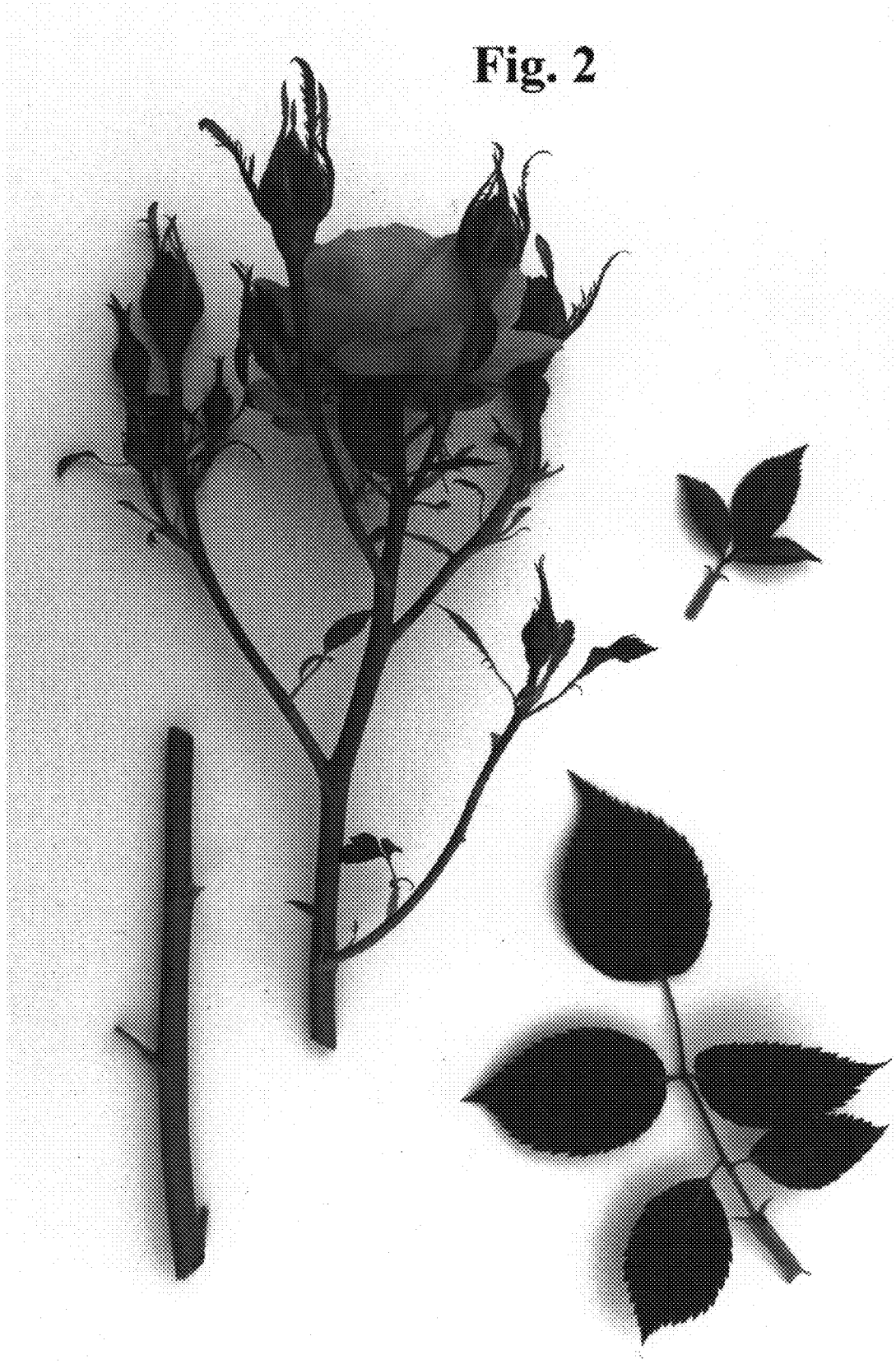

Specifically illustrated in FIG. 2 of the drawings are a cluster of flowers and flower buds attached to the branch, bare stems, mature and juvenile leaves. Plants shown are 2 years of age.

DETAILED DESCRIPTION OF THE VARIETY

The following is a description of 'Poulpah079',as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, characteristics of the rose variety 'Poulpah064', U.S. Plant Pat. No. 25,971 are compared to 'Poulpah079' in Chart 1.

CHART 1

| | 'Poulpah079' | 'Poulpah064' |
|---|---|---|
| Petal Count | 65 | 35 |
| Flower Diameter | 70 mm | 60 mm |
| General Tonality of Flower Color | Yellow-Orange Group 22B and Orange-Red Group 32B | Yellow-Orange Group 14C with intonations of Yellow-Orange Group 22B |

FLOWER AND FLOWER BUD

Blooming habit: Continuous.

Flower bud:

*Size.*—Upon opening, 22 mm in length from base of receptacle to end of bud. Bud diameter is 14 mm.

*Bud form.*—Ovoid.

*Bud color.*—As sepals divide petals are Orange-Red Group N34A, Yellow-Orange Group 21B, and Orange Group 28B.

*Sepal inner surface.*—Color: Green Group 138B, with intonations of Greyed-Purple Group 183C. Surface: Lightly pubescent.

*Sepal outer surface.*—Color: Yellow-Green Group 144A, with intonations of Greyed-Purple Group 183C. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—24 mm long, 9 mm wide.

*Receptacle.*—Texture: Smooth. Size: 11 mm in height, 11 mm wide. Color: Yellow-Green Group 144A. Shape: Campanulate.

*Pedicel.*—Surface: Rough. Length: 25 to 45 mm. Diameter: 3 mm on average. Color: Greyed-Red Group 181B with Yellow-Green Group 144A. Strength: Strong.

*Peduncle.*—Length: 40 to 45 mm. Diameter: About 3 mm. Color: Yellow-Green Group 144A with intonations of Greyed-Red Group 180A. Texture: Smooth.

Flower bud development: Flower buds are borne in clusters of about 10 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 70 mm when open. Flower depth is 35 mm.

*Flower shape.*—Open cup double flower, with petals that curve out from the center.

*Shape of flower, side view.*—The upper portion is flat. The lower portion is convex.

Petalage: Under normal conditions, flowers have about 65 petals.

General tonality of flower: Open flowers are a combination of Yellow-Orange Group 22B and Orange-Red Group 32B.

Petal color:

*Upon and after opening, outer petals.*—Upper surface: Yellow Orange 18A, and Yellow Group 13A, splashed with Orange Group 26B. Lower surface: Yellow Group 12A, splashed with Yellow-Orange Group 16C and Orange-Red Group 31B. Occasional streaks of Orange-Red Group N34C.

*Upon and after opening, inner petals.*—Upper surface: Yellow Orange 15D splashed with Yellow Group 12A. At the petal base, Yellow Group 13B. Lower surface: Yellow-Orange Group 18A, splashed with Orange-Red Group 32C. At the base, Yellow Group 12A.

Petals:

*Petal reflex.*—None.

*Margin.*—Entire and uniform. Very light undulations.

*Shape.*—Rounded. Apex shape: Rounded. Base shape: Acute and rounded.

*Size.*—30 mm (l)×30 mm (w).

*Texture.*—Smooth.

*Thickness.*—Average.

Petaloids:

*Size.*—13 mm (l) by 5 mm (w).

*Quantity.*—10 to 15.

*Shape.*—Elliptical with an acute base and rounded apices.

*Color.*—On the upper surface Yellow Orange 18A, and Yellow Group 13A, splashed with Orange Group 26B. The underside is Yellow Group 12A, splashed with Yellow-Orange Group 16C and Orange-Red Group 31B.

Reproductive flower parts:

*Pollen.*—None observed.

*Anthers.*—Size: 2 mm in length. Color: Yellow Group 12D. Quantity: 35 on average.

*Filaments.*—Color: Yellow Orange 14A. Length: 5 mm.

*Pistils.*—Length: 5 mm. Quantity: 20 on average.

*Stigmas.*—Color: Yellow-Green Group 154D.

*Styles.*—Color: Yellow-Green Group 154D.

*Location of stigmas.*—Inferior in location relative to the length of the filaments and the height of the anthers.

*Hips.*—None Observed.

PLANT

Plant growth: Upright, bushy and compact. Plants are 30 to 33 cm in height, and 40 cm wide.

Stems:

*Color of juvenile growth.*—Yellow-Green Group 144B.

*Color of mature growth.*—Yellow-Green Group 144B.

*Length.*—Canes are about 10 cm from the base of the plant to the flowering portion.

*Diameter.*—About 5 mm.

*Internodes.*—On mature canes about 35 mm between nodes.

*Surface texture.*—Young wood: Smooth. Older wood: Smooth.

Long prickles: None observed.

Plant foliage:

*Compound leaf.*—150 mm (l)×100 (w).

*Quantity.*—2 or 3 leaves per 10 cm of stem on average.

*Leaf bearing angle to the stem.*—45 degrees.

*Color of juvenile foliage.*—Upper side: Yellow-Green Group 146A. Lower side: Yellow-Green Group 146B with intonations of Greyed-Purple Group 183C.

*Color of mature foliage.*—Upper side: Yellow-Green Group 146A. Lower side: Yellow-Green Group 146B.

Plant leaves and leaflets:

*Stipules.*—Size: 25 mm long, 4 mm wide. Quantity: 2 per compound leaf. Shape: Linear, slightly broad based with outward extending apices. Margins: Finely serrated. Color: Yellow-Green Group 144B.

*Petiole.*—Length: About 50 mm. Diameter: 1.5 mm. Upper surface color: Yellow-Green Group 144A. Lower surface color: Yellow-Green Group 144B.

*Rachis.*—Length: 45 mm on average. Upper surface color: Yellow-Green Group 144A. Lower surface color: Yellow-Green Group 144B.

*Leaflet.*—Quantity: Normally 5 leaflets. Margins: Serrated. Size: Terminal leaflets are about 55 mm long, 45 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant named 'Poulpah079', substantially as illustrated and described herein, due to its abundant orange yellow flowers, disease resistance, and extended period of bloom.

* * * * *